United States Patent [19]

Sauke et al.

[11] Patent Number: 5,640,014

[45] Date of Patent: Jun. 17, 1997

[54] LASER DIODE SPECTROMETER FOR ANALYZING THE RATIO OF ISOTOPIC SPECIES IN A SUBSTANCE

[75] Inventors: Todd B. Sauke; Joseph F. Becker, both of San Jose; Jose de la Torre-Bueno, San Diego, all of Calif.

[73] Assignee: San Jose State University Foundation, San Jose, Calif.

[21] Appl. No.: 650,118

[22] Filed: May 22, 1996

Related U.S. Application Data

[63] Continuation of Ser. No. 440,636, May 15, 1995, Pat. No. 5,543,621.

[51] Int. Cl.[6] .................................................. G01N 21/00
[52] U.S. Cl. ..................... 250/339.03; 250/343; 250/345
[58] Field of Search ............................... 250/339.03, 345, 250/343

[56] References Cited

U.S. PATENT DOCUMENTS 5,173,749  12/1992  Tell et al. ................................ 356/437
5,543,621  8/1996  Sauke et al. ........................ 250/339.03

OTHER PUBLICATIONS

S. Lundqvist, J. Margolis, and J. Reid, "Measurements of pressure–broadening coefficients of NO and $O_3$ using a computerized tunable diode laser spectrometer." Applied Optics, vol. 21, No. 17 (Sep. 1, 1982) pp. 3109–3113.

Primary Examiner—Constantine Hannaher
Attorney, Agent, or Firm—John L. Rogitz

[57] ABSTRACT

A diode laser spectrometer includes a sample chamber for holding a sample gas, e.g., human breath, having first and second isotopic species in an unknown concentration ratio and a reference chamber for holding a reference gas having the first and second isotopic species in a known concentration ratio. Laser light is directed through both chambers at wavelengths corresponding to absorption wavelength of the isotopic species, and the light is detected and sample and reference signals generated. The signals are processed by a computer to determine the concentration ratio of the first isotopic species to the second isotopic species in the sample gas. The diode laser is cooled by a thermoelectric cooler or a cryocooler operating as a reverse Sterling engine.

8 Claims, 2 Drawing Sheets

LASER DIODE SPECTROMETER FOR ANALYZING THE RATIO OF ISOTOPIC SPECIES IN A SUBSTANCE

The present application is a continuation of U.S. patent application Ser. No. 08/440,636, filed May 15, 1995, now U.S. Pat. No. 5,543,621.

FIELD OF THE INVENTION

The present invention relates generally to laser-based spectroscopy, and more particularly to methods and apparatus for analyzing isotopic ratios in substances.

BACKGROUND

Carbon-13 ($^{13}C$) is a naturally occurring, non-radioactive isotope of Carbon, and $^{13}C$ makes up about 1% of all Carbon on Earth, with most of the remaining 99% of Carbon being composed of Carbon-12($^{12}C$). Measurements of the variations in the ratio of $^{13}C/^{12}C$ in substances can provide valuable information to biologists, geologists, and medical personnel because various processes affect the value of the ratio of $^{13}C/^{12}C$ in known ways.

As an example of one application wherein knowledge of the ratio of $^{13}C/^{12}C$ can be important, Carbon found in soil which includes organic matter from plant life has a relatively low $^{13}C/^{12}C$ ratio, compared to Carbon from inorganic sources. Consequently, it might be inferred whether a planet such as Mars has ever supported Carbon-based plant life by analyzing the $^{13}C/^{12}C$ ratio in various Martian soil samples.

As another example, human disease can be diagnosed by measuring the ratio $^{13}C/^{12}C$ in a patient's breath. Diagnosing disease by analyzing the $^{13}C$ content of breath affords many important advantages over other diagnostic tests, including safety, painlessness, quick results, and comparatively low cost.

To diagnose disease based upon $^{13}C$ analysis, a patient first ingests a capsule containing a food-like substance, referred to as a "substrate", which has been specifically isotopically enriched with $^{13}C$. Because different substrates are digested by different enzymes, it is possible to target particular organs for testing by tailoring the substrate to that organ. Indeed; many diseases may be diagnosed using such breath analysis, and a variety of substrates have been proposed or developed for medical diagnosis. Currently, these substrates include $^{13}C$ urea test for *Helicobacter pylori* bacteria in the gastrointestinal tract (a cause of ulcers and gastritis), $^{13}C$ galactose test for liver function and cirrhosis, $^{13}C$-Hiolein® test for fat malabsorption, $^{13}C$-Neolate® test for pancreatic and small intestine mucosal dysfunction, $^{13}C$ xylose test for small intestine bacterial overgrowth, $^{13}C$ glucose test for carbohydrate malabsorption, $^{13}C$ starch test for pancreatic amylase, $^{13}C$ protein test for protein metabolism, $^{13}C$-amino acids for inborn errors of metabolism, and $^{13}C$ lactose test for lactose intolerance. It will be appreciated that many more such tests with associated substrates may be developed.

Once ingested, the substrate is digested or otherwise processed by the targeted organ, and Carbon Dioxide ($CO_2$) resulting from the digestion is transported by the patient's venous blood to the patient's lungs, where the $CO_2$ is transferred through the alveolar walls of the lungs and exhaled. The ratio of $^{13}CO_2$ to $^{12}CO_2$ in the patient's breath is then measured by a special purpose instrument. Normal individuals will show a different ratio than individuals having the disease, thereby providing a diagnostic tool to the physician. Importantly, the underlying analytical technique-measuring the ratio of $^{13}CO_2$ to $^{12}CO_2$ in the patient's breath, remains the same for all the diseases which can be diagnosed in this fashion. Therefore, a single purpose instrument can perform a wide variety of tests, when used with different substrates.

Breath tests for diagnosing disease, however, are not yet in general use, primarily because of the high cost of instruments that are currently used for isotopic analysis. The most common such instruments are mass spectrometers, which are elaborate instruments with unit costs in the $150,000 to $500,000 range. Also, mass spectrometers typically require skilled technicians to operate. This makes breath testing economically impractical for widespread use in doctors' offices or hospitals.

Alternative analysis instruments which are less expensive than mass spectrometers accordingly have been introduced for measuring the ratio of $^{13}C/^{12}C$ in a patient's breath. More specifically, instruments have been introduced that employ the principles of optical spectroscopy to measure the ratio Of $^{13}C/^{12}C$ in a patient's breath. Optical spectroscopy is a method of measurement in which gaseous materials can be detected and measured by their ability to absorb optical energy at certain wavelengths. Each gaseous material has characteristic wavelengths at which it absorbs light energy. When multi-spectral light covering a range of wavelengths is transmitted from a light source through a gas, the composition of the gas is indicated by the specific wavelengths absorbed and the magnitude of the absorption.

Lasers are widely used as the light source in optical spectroscopy, owing to the narrow spectral emission line afforded by the use of coherent light. Of particular importance to the present invention are diode laser light sources. A diode laser is a class of laser based on semiconductor technology. It consists of several layers of different materials on a crystalline substrate, such as silicon, gallium arsenide, or lead sulfide. Diode lasers have the property of emitting light in a very narrow wavelength band when electrical current is applied to them.

An example of one such device is disclosed in U.S. Pat. No. Re. 33,493 to Lee et at. for a diode laser gas analysis spectrometer that operates at a wavelength of 3–6 µm. Because the primary (i.e., $v_3$ fundamental) absorption band for Carbon Dioxide is approximately 4.3 µm, the Lee et al. apparatus operates at an optimal wavelength for purposes of detecting the ratio of $C^{13}/C^{12}$. Unfortunately, the Lee et al. apparatus requires cryogenic cooling, rendering it inappropriate both for spacecraft uses and medical diagnostic uses.

An alternate diode laser-based spectrometer is disclosed in U.S. Pat. No. 5,317,156 to Cooper et al., which uses a diode laser made of indium-gallium-arsenide-phosphorus (InGaAsP) that can operate at room temperature and consequently does not require cryogenic cooling. Unfortunately, the Cooper et al. spectrometer has an operating wavelength of only 1.6 µm, which means that the absorption spectra it can detect is at a weaker band of Carbon Dioxide absorption, instead of the $v_3$ fundamental absorption band for Carbon Dioxide. Consequently, because the amount of absorption by Carbon Dioxide in the 1.6 µm region is orders of magnitude less than the amount of the absorption in the $v_3$ fundamental region, the Cooper et al. apparatus intrinsically suffers degraded sensitivity. As applied to breath analysis, sensitivity of measurement is an important parameter in a diode laser spectrometer, because using a less-sensitive instrument requires administering a greater dosage of $^{13}C$-bearing substrate to a patient, increasing costs and potentially complicating regulatory approval.

Accordingly, it is an object of the present invention to provide a spectrometer for analyzing the ratio of $^{13}C/^{12}C$ in a substance which operates at the 4.3 μm absorption wavelength region for Carbon Dioxide. Another object of the present invention is to provide a spectrometer for analyzing the ratio of $^{13}C/^{12}C$ in a substance which does not require cryogenic cooling. Still another object of the present invention is to provide a spectrometer for analyzing the ratio of $^{13}C/^{12}C$ in a substance which is easy to use and cost effective.

SUMMARY OF THE INVENTION

A spectrometer for analyzing the ratio of $^{13}C/^{12}C$ in a sample gas includes a laser diode illuminator for generating a first light beam characterized by a wavelength in the mid-infrared absorption range of $^{12}CO_2$ and a second light beam characterized by a wavelength in an absorption range of $^{13}CO_2$. The spectrometer also includes a primary thermoelectric cooler in thermal contact with the laser diode illuminator for maintaining a temperature of the illuminator at a predetermined temperature. Further, the spectrometer includes a sample chamber in light communication with the first and second light beams, wherein the sample chamber holds the sample gas. A sample detector is in light communication with the sample chamber for detecting light propagating therefrom and for generating a sample signal in response thereto, and a computer is electrically connected to the sample detector for receiving the sample signal and determining the ratio of $^{13}C/^{12}C$ in the sample gas in response.

Preferably, a reference detector and a reference chamber for holding a reference gas having a known ratio of $^{13}C/^{12}C$ are also provided. The reference chamber is in light communication with the illuminator and the reference detector, and the reference detector generates a reference signal representative of the ratio of $^{13}C/^{12}C$ in the reference chamber.

In the presently preferred embodiment, a null detector detects a light beam from the illuminator which does not propagate through either chamber. As intended by the present invention, the null detector generates a null signal, and both the null detector and the illuminator are disposed in a vacuum chamber.

Furthermore, a hollow heat exchanger holds the sample gas and maintains the sample gas above a predetermined temperature to thereby avoid the forming of condensation in the sample chamber. Additionally, the spectrometer includes a secondary thermoelectric cooler, a cold plate sandwiched between the primary and secondary thermoelectric coolers, and a heat sink in thermal contact with the secondary thermoelectric cooler and opposed to the cold plate relative to the secondary thermoelectric cooler. In the preferred embodiment, the cold plate, heat sink, and secondary thermoelectric cooler are held in juxtaposition by a plurality of fasteners.

According to the preferred embodiment, each fastener is formed with a respective head and a respective shank. The shank of each fastener is disposed in the cold plate, and the head of each fastener is juxtaposed with the heat sink and separated therefrom by a thermal insulator, such that the cold plate, secondary thermoelectric cooler, and heat sink are urged together when the thermoelectric coolers are energized to cool the laser diode illuminator.

The present spectrometer is computer operated, and the computer includes a program storage device readable by the computer and tangibly embodying a program of instructions executable by the computer to perform method steps for processing the sample signal, reference signal, and null signal. The method steps include normalizing the sample signal and reference signal with respect to the null signal, and then referencing the sample signal and reference signal to a known wavenumber axis. Further, the method steps include determining the absorbance at a first preselected wavelength in the sample signal and determining the absorbance at a second preselected wavelength in the reference signal, and determining the ratio of $^{13}C/^{12}C$ in the sample gas relative to the reference gas.

Preferably, the spectrometer includes a temperature sensor that is positioned adjacent to the laser diode illuminator for generating a temperature signal representative of the temperature thereof. The computer receives the temperature signal and controls energization of the primary thermoelectric cooler in response thereto.

In another aspect of the present invention, a spectrometer is disclosed for measuring the ratio of a first isotopic species in a sample gas to a second isotopic species in the sample gas. The spectrometer includes a sample chamber for holding the sample gas and a laser for emitting coherent light in a plurality of discrete wavelengths through the sample chamber. Also, the spectrometer includes an electrically powered cooler in thermal contact with the laser for establishing a predetermined temperature of the laser. A sample detector for detecting light from the sample chamber and generating a sample signal in response thereto is provided, and a computer is associated with the sample detector for receiving the sample signal and determining the ratio of the first isotopic species to the second isotopic species in response thereto.

In still another aspect of the present invention, a program storage device is readable by a computer and tangibly embodies a program of instructions which are executable by the computer to perform method steps for processing a sample signal representative of isotopic species ratios in a sample gas, a reference signal representative of isotopic species ratios in a reference gas, and null signal. The signals are generated by a diode laser spectrometer, and the method steps include normalizing the sample signal and reference signal with respect to the null signal, and then referencing the sample signal and reference signal to a known wavenumber axis. Next, the absorbance at a preselected wavelength for each isotopic species in the sample signal and the absorbance at the same wavelengths for each isotopic species in the reference signal are determined. Then, the ratio of preselected isotopic species in the sample gas relative to the reference gas is determined.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
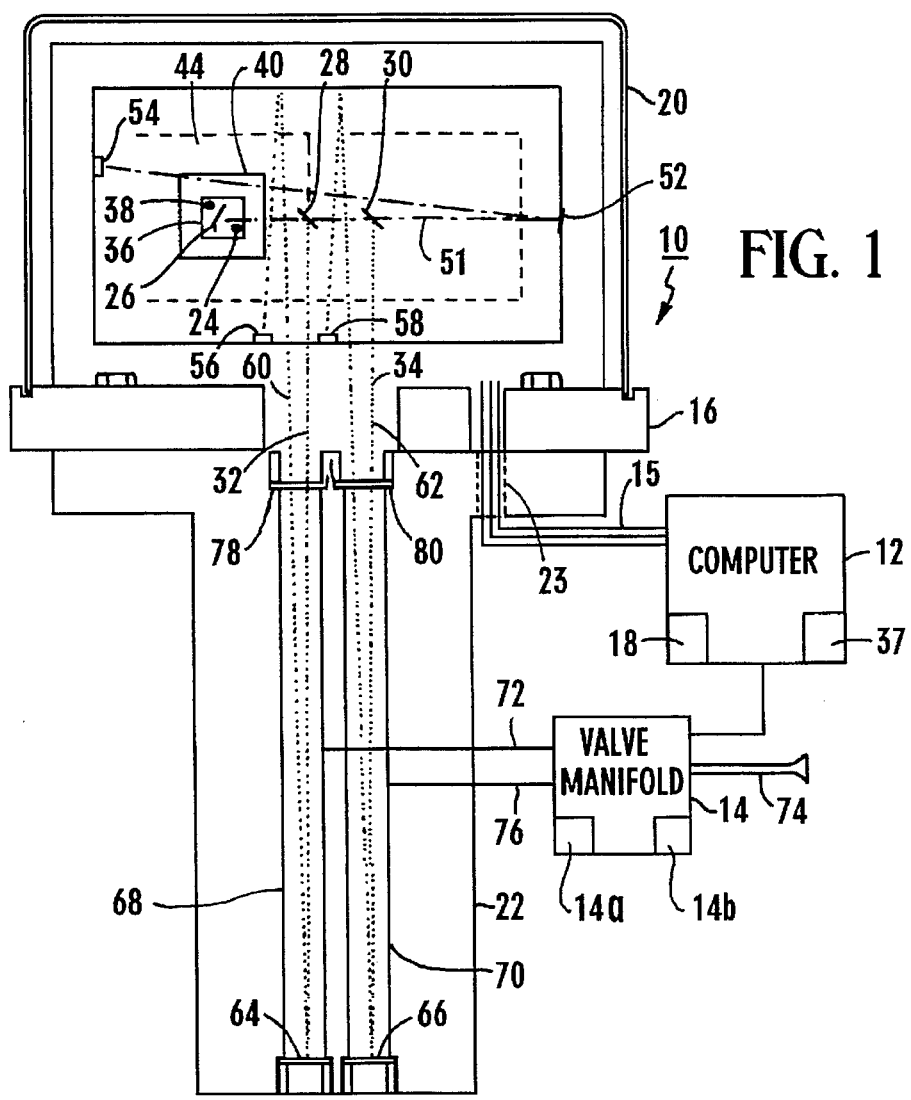
FIG. 1 is a schematic top view of the spectrometer of the present invention, with the electrical lines inside the vacuum chamber removed for clarity.

Initially referring to FIG. 1, a diode laser spectrometer is shown, generally designated 10. As shown, the spectrometer 10 is a spectrophotometer which includes a computer 12 that is electrically connected to a valve manifold 14 for controlling the operation of valves therein. The valve manifold 14 also preferably includes a vacuum pump 14A and a source 14B of reference gas. Further, the computer 12 is electrically connected via a plurality of electrical lines 15 to components within a housing 16 to control the operation of the components as disclosed below. It is to be understood that the computer 12, valve manifold 14, and housing 16 can all be included in a single casing.

In one preferred embodiment, the computer 12 is a laptop computer which includes a Pentium® central processor and a program storage device 18. As intended by the present invention, the program storage device 18 may be implemented by a processor within the computer 12 that executes a series of computer-executable instructions. These instructions may reside, for example, in RAM of the computer 12.

Alternatively, the instructions may be contained on a data storage medium, such as a computer diskette. Or, the instructions may be stored on a DASD array, magnetic tape, conventional hard disk drive, electronic read-only memory, optical storage device, or other appropriate data storage device. In an illustrative embodiment of the invention, the computer-executable instructions may be lines of compiled $C^{++}$ language code.

In the preferred embodiment shown in FIG. 1, the housing 16 includes a vacuum chamber 20 and a cell assembly 22, and the electrical lines 15 pass into the vacuum chamber 20 through a vacuum lock fitting 23. In accordance with the present invention, the vacuum chamber 20 is evacuated during manufacturing and then sealed. A diode laser 24 is positioned in the vacuum chamber 20 in optical communication with the cell assembly 22. More particularly, a concave reflective mirror 26 is positioned to reflect light from the diode laser 24 to sample and reference beam splitters 28, 30, which in turn reflect respective sample and reference input beams 32, 34 into the cell assembly 22. In one preferred embodiment, the beam splitters 28, 30 are polypropylene/polyethylene pellicle beamsplitters. It is to be understood that the diode laser 24 is also electrically connected to the computer 12 via one of the lines 15, and the computer 12 establishes an electric current flow through the diode laser 24 as appropriate for the desired frequency of the output beam of the diode laser 24.

Preferably, the diode laser 24 is a tunable lead-salt diode laser with an operating temperature above seventy seven Kelvin (77 K.) and an emission spectrum of about three micrometers to twelve micrometers (3 μm–12 μm), with a monochromatic coherent light beam output that can be swept in frequency by varying the input electrical current to the diode laser 24. More preferably, the diode laser 24 has an operating temperature greater than 200 K. and a light beam output the wavelength of which can be swept in the 4.3 μm region. In the preferred embodiment, the diode laser 24 is a buried heterostructure-type diode laser made by Laser Photonics of Andover, Mass. and composition tuned to operate in the 4.2 μm–4.4 μm (2280–2380 $cm^{-1}$) spectral region.

To establish a constant predetermined temperature of the diode laser 24, an electric cooler 36 is positioned in thermal contact with the diode laser 24. As shown in FIG. 1, the diode laser 24 is physically mounted on the electric cooler 36. In one presently preferred embodiment, the electric cooler 36 is a primary thermoelectric cooler, and indeed may be a stack of individual thermoelectric coolers. In an alternate embodiment, the electric cooler 36 is a cryocooler, such as one of the cryocoolers made by Sunpower Inc. of Athens, Ohio. As intended by the present invention, a cryocooler is a reverse Sterling engine with an electric linear induction motor coupled to a piston for pumping a cooling fluid through a sealed cycle in the cooler. In either case, it will be appreciated that the present invention avoids the use of conventional cryogenic cooling, rendering the present invention suitable both for spacecraft applications and medical diagnostic applications.

Like the diode laser 24, the electric cooler 36 is electrically connected to the computer 12, which controls the operation of the cooler 36 to establish a predetermined temperature of the diode laser 24. To this end, the computer 12 can incorporate a cryostat 37, e.g., one of the cryostats made by Laser Photonics. To provide a temperature feedback signal to the computer 12, a diode temperature sensor 38 is mounted on the electric cooler 36 to sense the temperature of the cooler 36 and generate a temperature feedback signal in response thereto. The diode temperature sensor 38 is electrically connected to the computer 12 via one or more of the lines 15 for sending the temperature feedback signal to the computer 12. Alternatively, the computer 12 can control the operation of a heater 39 which in turn is in thermal contact with the cooler 36 to thereby establish a predetermined temperature of the diode laser 24.

Figure 2:
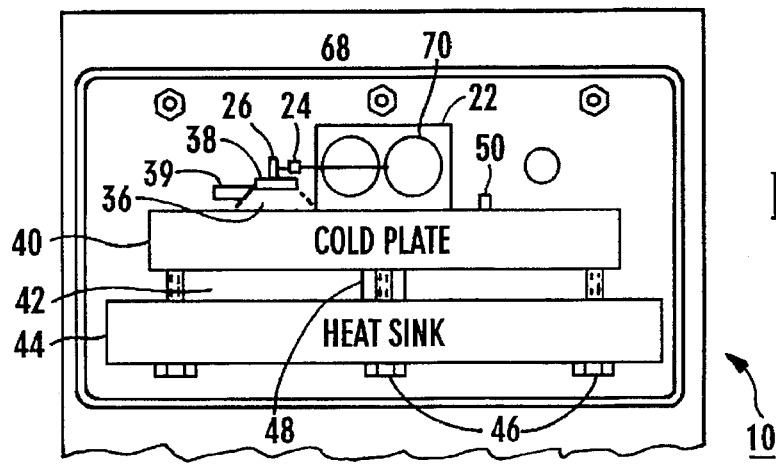
FIG. 2 is a schematic front view of the spectrometer of the present invention, with the computer and valve manifold removed for clarity.
Figure 3:
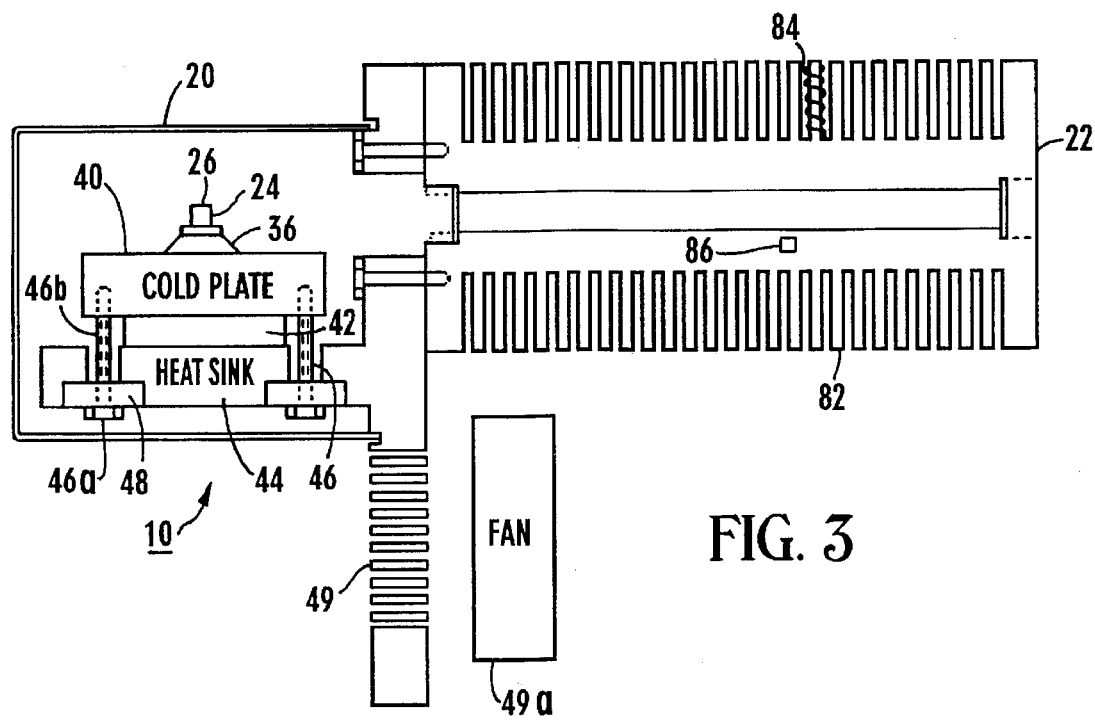
FIG. 3 is a schematic side view of the spectrometer of the present invention, with the computer and valve manifold removed for clarity.

In cross-reference to FIGS. 1, 2, and 3, when the primary electric cooler 36 is a thermoelectric cooler, an aluminum, steel, or copper cold plate 40 is positioned against the primary electric cooler 36, with the electric cooler 36 mounted on the cold plate 40. Also, a secondary thermoelectric cooler 42 is positioned in thermal contact with the cold plate 40, and an aluminum, steel, or copper heat sink 44 is positioned in thermal contact with the secondary cooler 42. As shown, a plurality of fasteners 46, preferably threaded bolts, hold the heat sink 44 against the secondary cooler 42 and also hold the secondary cooler 42 against the cold plate 40. The fasteners 46 are threadably engaged with complementarily-shaped structures in the cold plate 40, but the fasteners 46 are not in thermal contact with any other metallic component.

Stated differently, the cold plate 40 is sandwiched between the primary and secondary thermoelectric coolers 36, 42, and the cold plate 40 is in thermal contact with the coolers 36, 42 with the heat sink 44 being opposed to the cold plate 40 relative to the secondary thermoelectric cooler 42. The cold plate 40, heat sink 44, and secondary thermoelectric cooler 42 are held in juxtaposition by the fasteners 46.

As perhaps best shown in cross-reference to FIGS. 2 and 3, each fastener 46 includes a respective shank 46a and a respective head 46b. The shank 46b of each fastener 46 is disposed in the heat sink 44, secondary thermoelectric cooler 42, and cold plate 40. Further, the head 46a of each fastener 46 is juxtaposed with the heat sink 44 and is separated therefrom by a respective thermal insulator 48. The skilled artisan will appreciate that with the orientation of the fasteners 46 as shown, owing to thermal expansion characteristics of metal, the fasteners 46 effectively tighten, vice loosen, when the electric coolers 36, 42 are energized. Thereby, the cold plate 40, secondary thermoelectric cooler 42, and heat sink 44 are urged more tightly together to improve heat transport away from the electric coolers 36, 42 when the electric coolers 36, 42 are energized.

FIG. 2 shows that a cold plate temperature sensor 50 advantageously can be mounted on the cold plate 40 and electrically connected to the computer 12 to provide the computer 12 with an additional temperature feedback signal. The sensor 50 can be a thermistor or other appropriate temperature sensor. FIG. 3 shows that the heat sink 44 is in thermal contact with cooling fins 49, which are cooled by a fan 49A, to remove heat from the heat sink 44.

Referring back to FIG. 1, a null beam portion 51 of the output beam of the diode laser 24 propagates through the beam splitters 28, 30 and is reflected by a null mirror 52 to a null detector 54, both of which are positioned in the vacuum chamber 20. As shown, the null beam portion 51 does not enter the cell assembly 22. Additionally, sample and reference detectors 56, 58 are positioned in the vacuum chamber 20 for receiving respective sample and reference return beams 60, 62 from the cell assembly 22. It is to be understood that all three detectors 54, 56, 58 generate respective electrical null, sample, and reference signals representative of the light which respectively impinges upon them, and that the detectors 54, 56, 58 are electrically connected to the computer 12 for sending their respective signals to the computer 12.

In one embodiment, the detectors 54, 56, 58 are Indium-Antimonide (InSb) detectors made by InfraRed Associates of Cranbury, N.J., although other suitable infrared detectors, e.g., Mercury-Cadmium-Tellurium (HgCdTe) detectors can be used. The detectors 54, 56, 58 are mounted on one of the metallic heat transfer components 36, 40, 42, 44 disclosed above for establishing a predetermined temperature of the detectors 54, 56, 58. Accordingly, the computer 12 may include or have accessible to it transimpedance amplifiers which are dc-coupled to the detectors 54, 56, 58, and the amplifiers are connected to a 12-bit, 100 kHz analog-to-digital converter board of the computer 12. In one presently preferred embodiment, the converter board can be a Model CIO-AD16/F board made by Computer Boards of Mansfield, Mass.

Recall that the sample and reference detectors 56, 58 receive respective sample and reference return beams 60, 62. As shown in FIG. 1, the sample and reference return beams 60, 62 are the reflections, from respective sample and reference mirrors 64, 66 that are disposed in respective hollow cylindrical sample and reference cells 68, 70 of the cell assembly 22, of the sample and reference input beams 32, 34.

As intended by the present invention, the sample cell 68 defines a sample chamber that holds a sample gas having first and second isotopic species in an unknown concentration. In contrast, the reference cell 70 defines a reference chamber that holds a reference gas having the first and second isotopic species in a known concentration. It is the purpose of the present invention to determine the ratio of the concentration of the first isotopic species in the sample gas to the concentration of the second isotopic species in the sample gas. The sample gas may be selected from any gas for which it is desired to measure isotopic ratios. In a preferred embodiment, the sample gas is a mixture of $^{13}CO_2$ and $^{12}CO_2$, and the isotopic species ratio sought is $^{13}C/^{12}C$.

Preferably, the chambers of both cells 68, 70 are first evacuated then filled with sample and reference gases, and the cells 68, 70 are in thermal contact with each other to minimize temperature differences between them. The valve manifold 14 is in fluid communication with the sample cell 68 via a fluid line 72, for selectively porting sample gas into the sample chamber. To collect the sample gas from, e.g., a human patient's breath, fluid communication can be established between the valve manifold 14 and a sample collection tube 74, into which the patient's breath can be directed.

If desired, fluid communication can also be established between the reference cell 70 and the valve manifold 14 via a fluid line 76, to recharge the reference cell 70 with reference gas from the source 14B or evacuate the reference cell by appropriately operating the vacuum pump 14A. Indeed, the present invention envisions that the reference cell 70 and null beam portion 51 can be omitted and the sample cell 68 alternately charged with sample gas, evacuated, and recharged with reference gas to assume the functions of the reference cell 70 and null beam portion 51.

Still referring to FIG. 1, the sample cell 68 and reference cell 70 are separated from the vacuum chamber 20 by respective infrared transparent sample and reference optical windows 78, 80. The windows allow the input sample and reference beams 32, 34 to enter the sample and reference chambers and respectively propagate to the sample and reference mirrors 64, 66, from where they are reflected back as the sample and reference return beams 60, 62.

As the beams propagate through the sample and reference cells 68, 70, they are partially absorbed by the gases therein, and the characteristics of their absorption is affected by the concentrations of the first and second isotopic species in the gases. Consequently, the beams can be detected by the sample and reference detectors 56, 58 and the characteristics of their absorption analyzed by the computer 12 to determine the ratio of the concentration of the first isotopic species to the concentration of the second isotopic species.

FIG. 3 best shows that the cell assembly 22 includes a hollow heat exchanger 82. The heat exchanger 82 holds the sample gas prior to porting the sample gas to the sample chamber. In accordance with the preferred embodiment, the heat exchanger 82 is in thermal contact with the heat sink 44 and is warmed thereby, to maintain the sample gas above a predetermined temperature to thereby avoid the forming of moisture condensation in the sample chamber. If desired, computer 12-controlled electric coils 84 can be disposed in thermal contact with the heat exchanger 82 to heat the heat exchanger 84. A heat exchanger temperature sensor 86 is mounted on the heat exchanger 82 to generate a signal representative of the temperature of the heat exchanger 82, and the signal from the temperature sensor 86 is sent to the computer 12.

Figure 4:
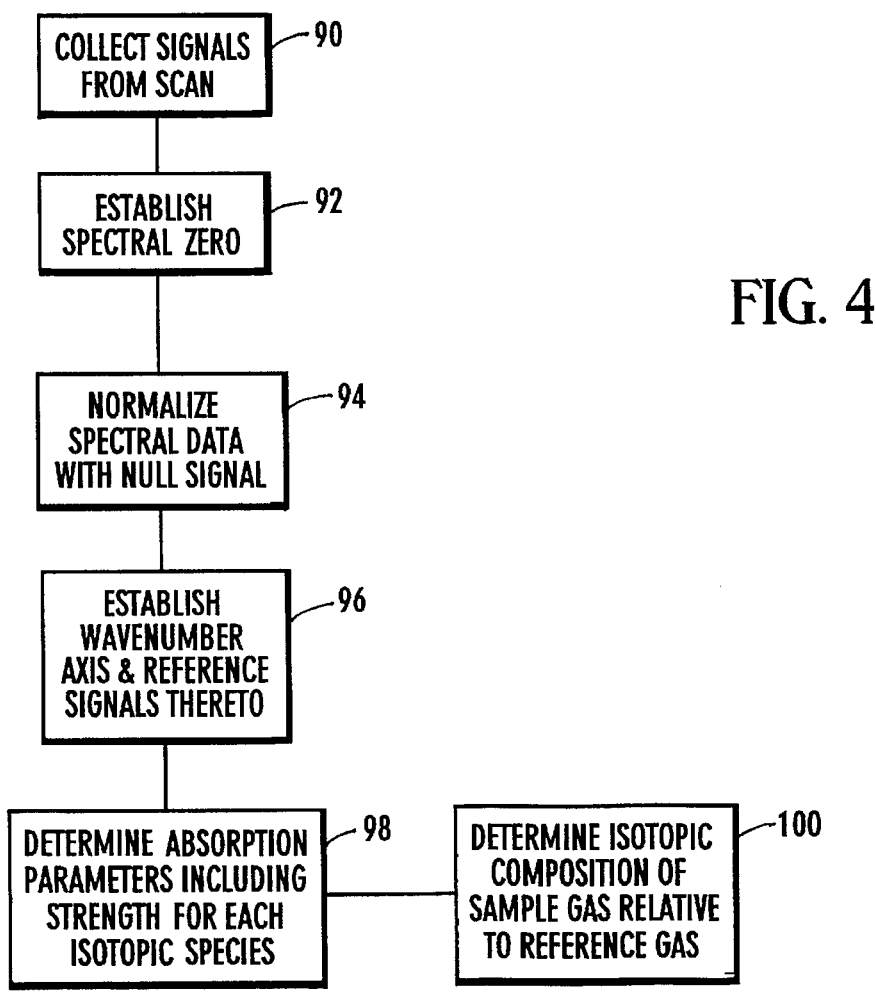
FIG. 4 is a flow chart showing the analytical steps of the present invention.

Now referring to FIG. 4, in the operation of the spectrometer 10, the computer 12 first initiates a scan at block 90 and collects the reference, null, and sample signals resulting therefrom. In generating the scan, the computer 12 causes electrical current to pass through the diode laser 24 as appropriate to cause the diode laser 24 to emit laser light in at least two frequencies corresponding to light absorption frequencies of the first and second isotopic species, respectively.

In other words, for each scan cycle the computer 12 causes the diode laser 24 to generate a first light beam characterized by a wavelength corresponding to a mid-infrared absorption frequency of the first isotopic species and a second light beam characterized by a wavelength corresponding to a mid-infrared absorption frequency of the second isotopic species. It is to be understood that the input current can be swept in magnitude to cause the diode laser 24 to sweep the absorption spectrum of interest, and that a single scan can represent the average of a plurality of sweeps, e.g., 512.

When the first isotopic species is $^{13}C^{16}O^{16}O$ and the second isotopic species is $^{12}C^{16}O^{16}O$, the absorption spectrum of interest is from 2280 cm$^{-1}$ to 2380 cm$^{-1}$, and the first and second light beams are preferably characterized by frequencies of 2291.681 cm$^{-1}$ and 2291.542 cm$^{-1}$, respectively, corresponding to the R(10) line of $^{13}$C and the P(60) line of $^{12}$C in the $v_3$ mid-infrared band. These lines are selected because they are close to each other, simplifying the required wavelength sweep, and because the absorptions for the two lines by $^{13}CO_2$ and $^{12}CO_2$, respectively, are about equal, thereby improving the accuracy of the ratio measurement. The diode laser 24 may be pulsed at a reduced duty cycle, e.g., about 10%, to reduce the heat load on the primary electric cooler 36.

As discussed above, the return beams 60, 62 which propagate through the sample and reference cells 68, 70 are detected by the sample and reference detectors 56, 58. The signals from the detectors 56, 58, along with the signal from the null detector 54 which is nearly simultaneously collected with the sample and reference signals, are sent to the computer 12.

After receiving the sample, reference, and null signals, the computer 12 proceeds to block 92, wherein the computer 12 establishes a spectral zero to correct for thermal and electronic drift. To establish a spectral zero, the signals from the detectors 54, 56, 58 are measured when the diode laser 24 is not activated to establish respective zero signals. Then, the zero signals are subtracted from the respective sample, reference, and null signals sensed when the diode laser 24 is activated. Alternatively, the input light beams 32, 34 periodically can be mechanically blocked by a shutter (not shown) in synchrony with the spectral scan.

It happens that the intensity of the input beams 32, 34 may not always be precisely known. Accordingly, the present invention addresses this problem at block 94, wherein the computer 12 normalizes the sample signal from the sample detector 56 and reference signal from the reference detector 58 with respect to the null signal from the null detector 54 by dividing the sample and reference signals by the null signal.

Then, at block 96, the computer 12 establishes a wavenumber axis and references the sample signal and reference signal to the wavenumber axis. In the preferred embodiment, the computer 12 assembles a first array of numbers which represents known relative or absolute wavenumbers. Additionally, the computer 12 assembles a second array of numbers which represents spectral markers in the spectrum of interest.

In assembling the second array, the computer 12 essentially identifies absorption peaks in one of the sample or reference signals that have well-known locations. These peaks establish the entries in the second array. Alternatively, an etalon (not shown) and a fourth detector (not shown) can be incorporated in the spectrometer 10 to generate known, equally spaced interference fringes that serve as the marker peaks which establish the second array.

Then, the computer 12 iteratively fits a smooth curve through the first and second arrays, effectively shifting the arrays as appropriate to smooth the curve. In one presently preferred embodiment, the curve is represented by a polynomial equation, and the polynomial equation is expanded to reference the wavenumber axis to the absorption spectra data represented by the sample and reference signals.

Next, at block 98, the computer 12 determines the absorption parameters of the absorption peaks of interest for each of the isotopic species. Each absorption peak is characterized by a so-called Voigt function, and at block 98 the computer 12 determines certain characteristics of the Voigt functions that represent the absorption peaks of interest, to thereby determine the amount of absorption at that frequency peak. The characteristics sought are absorption strength, position relative to the wavenumber axis, Gaussian width, and Lorentzian width. While only the first parameter, absorption strength, is used in calculating the concentration ratio of the isotopic species, the other three parameters are required in determining absorption strength.

In the presently preferred embodiment, the computer 12 uses the so-called Levenberg-Marquardt engine to determine the characteristics of Voigt functions rising a non-linear least squares fit of the data. The computer 12 provides the engine with the Voigt function transmittance equation (and its derivative with respect to each variable) as follows:

transmittance($v$)=B($v$)+Exp($-\Sigma_i(S_i*V(D_i, L_i, v-v_i))$),
where V is the Voigt function convolution of a Gaussian function of width D with a Lorentzian function of width L, B is a linear baseline function to account for instrument imperfections, S is the integrated absorbance (i.e., strength) of a given spectral line, $v_i$ is the center frequency of the $i^{th}$ absorption line, and the sum is the sum of all absorption lines in the spectrum.

Based upon the sample and reference signal data and the equations provided it, along with initial estimates for each of the parameters, the Levenberg-Marquardt engine conducts a non-linear least squares fit to iteratively update calculated Voigt parameters by iteratively fitting the calculated spectrum with the spectrum as measured. Once the improvement in the difference between the calculated fit and measured spectrum is less than a predetermined value, the engine returns a calculated curve representative of each absorption peak of interest. During the iterative fitting process, the calculated curve can be convoluted with an instrument-unique function representative of the peculiarities of the spectrometer 10 in accordance with well-known convolution techniques to arrive at a final equation that represents the particular absorption peak sought.

Then, at block 100, the computer 12 determines the isotopic concentration of the sample gas with respect to the reference gas as follows:

$$R = \frac{(\text{Strength}(^{13}C, \text{sample})/\text{Strength}(^{12}C, \text{sample}))}{(\text{Strength}(^{13}C, \text{reference})/\text{Strength}(^{12}C, \text{reference}))}$$

wherein R is the ratio sought, and the strength numbers are the Voigt function strengths calculated above.

Thus, at block 98, the computer 12 determines the strength of at least one preselected absorption line for each isotopic species in each of the sample signal and reference signal, and then, at block 100, determines the ratio of the first species to the second species (e.g., $^{13}C/^{12}C$) in the sample gas relative to the reference gas.

While the particular LASER DIODE SPECTROMETER FOR ANALYZING THE RATIO OF ISOTOPIC SPECIES IN A SUBSTANCE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A spectrometer for measuring the ratio of a first isotopic species in a sample gas to a second isotopic species in the sample gas, comprising:

a sample chamber for holding the sample gas;

a laser for emitting coherent light in a plurality of discrete wavelengths through the sample chamber;

a cooler in thermal contact with the laser for establishing a predetermined temperature of the laser;

a sample detector for detecting light from the sample chamber and generating a sample signal in response thereto; and a computer associated with the sample detector for receiving the sample signal, wherein the spectrometer generates a null signal and a reference signal representative of the absorbance of a reference gas, and the computer includes a program storage device readable by the computer and tangibly embodying a program of instructions executable by the computer to perform method steps for processing the sample signal, reference signal, and null signal, the method steps comprising:

normalizing the sample signal and reference signal with respect to the null signal;

determining the strength of at least one preselected absorption line for each isotopic species in each of the sample signal and reference signal; and determining the ratio of the first isotopic species to the second isotopic species in the sample gas relative to the reference gas.

2. The spectrometer of claim 1, wherein the cooler is a cryocooler.

3. The spectrometer of claim 1, wherein the cooler is a primary thermoelectric cooler.

4. The spectrometer of claim 3, further comprising a reference detector and a reference chamber for holding a reference gas having a known ratio of the first isotopic species to the second isotopic species, the reference chamber being in light communication with the illuminator and the reference detector, the reference detector generating a reference signal representative of the known ratio in the reference chamber.

5. The spectrometer of claim 4, further comprising a null detector for detecting a light beam from the illuminator which does not propagate through either chamber and generating a null signal in response thereto, the null detector being electrically connected to the computer, the null detector and illuminator being disposed in a vacuum chamber.

6. The spectrometer of claim 1, further comprising a temperature sensor positioned adjacent to the laser for generating a temperature signal representative of the temperature thereof, the temperature sensor being electrically connected to the computer, the computer receiving the temperature signal and controlling the cooler in response thereto.

7. A spectrometer for measuring the ratio of a first isotopic species in a sample gas to a second isotopic species in the sample gas, comprising:

a sample chamber for holding the sample gas;

a laser for emitting coherent light in a plurality of discrete wavelengths through the sample chamber;

a primary thermoelectric cooler in thermal contact with the laser for establishing a predetermined temperature of the laser;

a secondary thermoelectric cooler, a cold plate sandwiched between the primary and secondary thermoelectric coolers and in thermal contact therewith, and a heat sink in thermal contact with the secondary thermoelectric cooler and opposed to the cold plate relative to the secondary thermoelectric cooler;

a sample detector for detecting light from the sample chamber and generating a sample signal in response thereto; and a computer associated with the sample detector for receiving the sample signal and determining the ratio of the first isotopic species to the second isotopic species in response thereto.

8. The spectrometer of claim 7, wherein the cold plate, heat sink, and secondary thermoelectric cooler are held in juxtaposition by a plurality of fasteners, each fastener is formed with a respective head and a respective shank, and the shank of each fastener is disposed in the cold plate, and the head of each fastener is juxtaposed with the heat sink and separated therefrom by a thermal insulator, such that the cold plate, secondary thermoelectric cooler, and heat sink are urged together when the thermoelectric coolers are energized to cool the laser.

* * * * *